United States Patent
Wolff et al.

(10) Patent No.: US 6,562,367 B1
(45) Date of Patent: *May 13, 2003

(54) TRANSDERMAL THERAPEUTIC SYSTEM (TTS) FOR ADMINISTERING SEXUAL STEROID HORMONES

(75) Inventors: Hans-Michael Wolff, Monheim (DE); Christoph Arth, Dusseldorf (DE)

(73) Assignee: Schwarz Pharma AG, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/462,033

(22) PCT Filed: Jun. 29, 1998

(86) PCT No.: PCT/EP98/03950
§ 371 (c)(1), (2), (4) Date: Mar. 16, 2000

(87) PCT Pub. No.: WO99/01116
PCT Pub. Date: Jan. 14, 1999

(30) Foreign Application Priority Data

Jul. 4, 1997 (DE) .......................... 197 28 517

(51) Int. Cl.⁷ .......................... A61F 13/00; A61K 9/14; A61L 15/16

(52) U.S. Cl. .......................... 424/449; 424/484; 424/487; 424/448; 424/443

(58) Field of Search .......................... 424/449, 448, 424/443

(56) References Cited

U.S. PATENT DOCUMENTS

| | | | |
|---|---|---|---|
| 5,730,999 A | * | 3/1998 | Lehmann et al. |
| 6,063,399 A | * | 5/2000 | Assmus et al. |
| 6,139,868 A | * | 10/2000 | Hoffmann |
| 6,165,499 A | * | 12/2000 | Kleinsorgen et al. |

FOREIGN PATENT DOCUMENTS

| EP | 0 563 507 A1 | 10/1993 | |
|---|---|---|---|
| EP | 0563 507 | * 10/1993 | ............ A61K/9/70 |
| EP | 0 848 960 A2 | 6/1998 | |

* cited by examiner

Primary Examiner—Thurman K. Page
Assistant Examiner—Isis Ghali
(74) Attorney, Agent, or Firm—Marshall, Gerstein & Borun

(57) ABSTRACT

A transdermal therapeutic system for transcutaneous administration of sexual steroid hormones over long time periods, and a solvent-free method for the production thereof, is disclosed. The steroid hormones are subjected to as little thermal exposure as possible, thereby avoiding decomposition of the steroid hormones.

12 Claims, 1 Drawing Sheet

Key to Figure:
abscissa: time (h)
on the right:
- ◆ - Example 1
- ■ - Example 2
- ▲ - Comparison Example
- ✕ - commercial preparation Estradiol plasma concentrations
Mean value curves (n = 8)

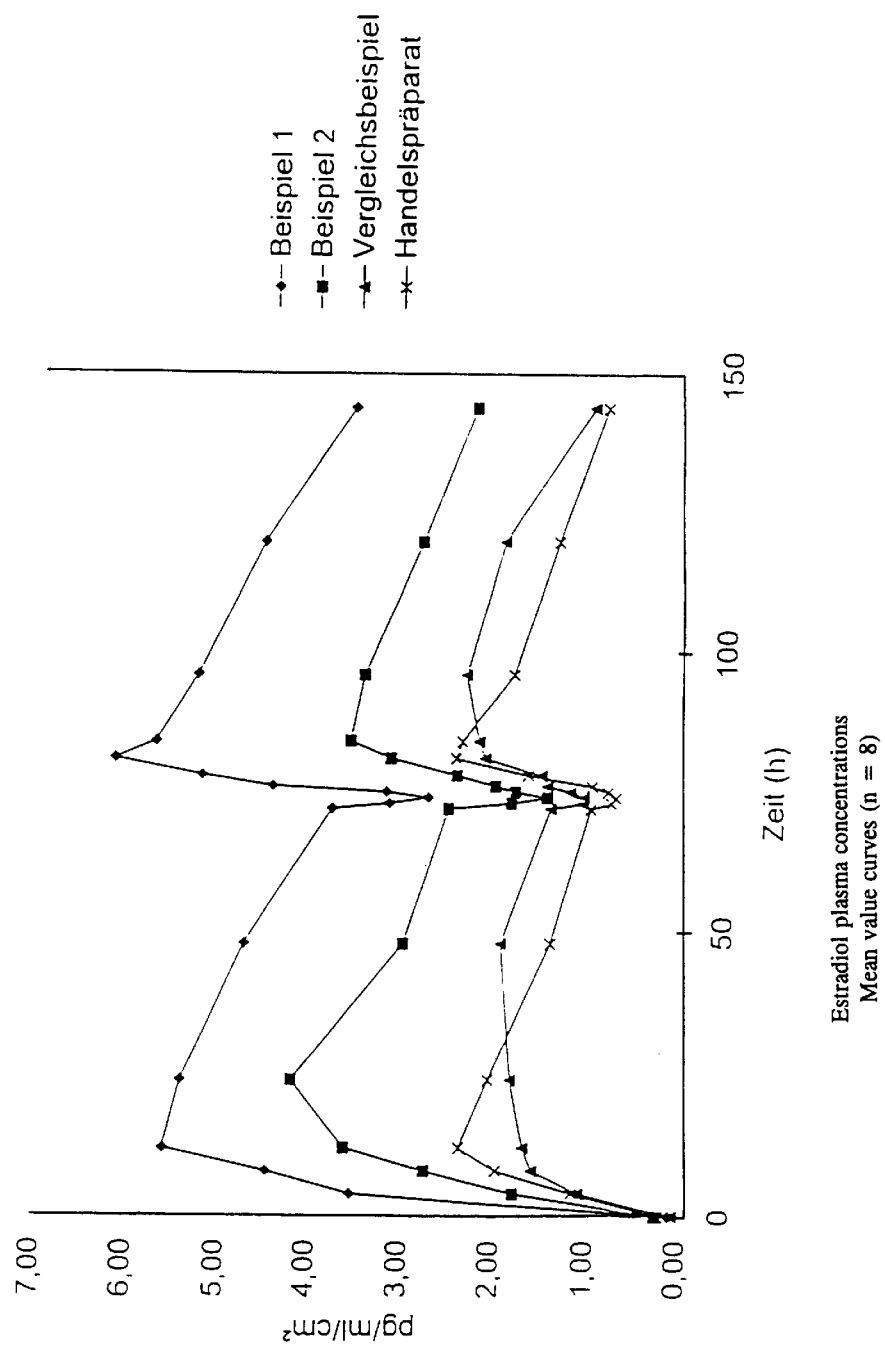

TRANSDERMAL THERAPEUTIC SYSTEM (TTS) FOR ADMINISTERING SEXUAL STEROID HORMONES

DESCRIPTION

The present invention concerns a Transdermal Therapeutic System (TTS) for the administration of steroid sex hormones alone or with other steroid sex hormones through the skin over a long period of time, as well as a method for its production without the use of solvents, the method being especially protective for the active ingredient.

The bioavailability of orally administered active ingredients is frequently unsatisfactory. Metabolization of many active ingredients in the liver can lead during the first passage through the liver to undesirable concentration relationships, toxic by-products and to the reduction of the activity and even to loss of activity. In comparison to oral administration, transdermal administration of active ingredients has various advantages. The introduction of the active ingredient can be controlled better over a longer period of time as a result of which high fluctuations in blood level are avoided. In addition, the required therapeutically effective dose can mostly be reduced significantly. In addition, patients frequently prefer a plaster to tablets, which must be taken once or several times daily.

In the past, in order to overcome the disadvantages of nontransdermal administration of active ingredients mentioned above, a number of transdermal therapeutic systems (TTS) with different structure were proposed for various active ingredients for the therapy of different diseases.

Thus, the technical documents given below describe a broad variety of systemically or locally reacting active ingredients, the parenteral administration of which is either based on dose-controlled or generally releasing systems.

For example, these are: U.S. Pat. Nos. 3,598,122; 3,598,123; 3,731,683; 3,797,494; 4,031,894; 4,201,211; 4,286,592; 4,314,557; 4,379,454; 4,435,180; 4,559,222; 4,568,343; 4,573,995; 4,588,580; 4,645,502; 4,702,282; 4,788,062; 4,816,258; 4,849,226; 4,908,027; 4,943,435 and 5,004,610.

In the late sixties of this century, it was assumed originally theoretically that all active ingredients with short half-life but high activity and good penetration through the skin would be suitable for safe and effective administration via a TTS. These early expectations regarding the possibilities of transdermal administration of active ingredients by TTS could, however, not be fulfilled. The reason for this is mainly that the skin is equipped naturally with an unassessable variety of properties in order to maintain its function as an intact barrier to the penetration of substances that are foreign to the body. (See in this regard: Transdermal Drug Delivery: Problems and Possibilities, B. M. Knepp et al., CRC Critical Review and Therapeutic Drug Carrier Systems, Vol. 4, Issue 1 (1987).)

Therefore, transdermal administration is available only for those few active ingredients which have a suitable combination of many favorable characteristics. For a given active ingredient, all the required characteristics that permit safe and effective transdermal administration cannot be predicted, either theoretically or practically.

The requirements for an active ingredient suitable for transdermal administration are the following:

permeability through the skin,
no adverse influence on the adhesiveness of the plaster by the active ingredient,
avoidance of skin irritations,
avoidance of allergic reactions,
favorable pharmacokinetic properties,
favorable pharmacodynamic properties,
relatively broad therapeutic window,
metabolic properties which are consistent with therapeutic application with continuous administration.

Undoubtedly, the above list of requirements is not exhaustive. In order to have an active ingredient available for transdermal application, the "correct" combination of all these requirements is desirable.

What was said above for the active ingredient applies similarly to the TTS composition containing the particular ingredient and to its structure.

Usually, transdermal therapeutic systems (TTS) are plasters which are equipped with an impermeable cover layer, a removable protective layer and a matrix which contains the active ingredient or a reservoir with semipermeable membrane, which contains the active ingredient. In the first case, they are called matrix plasters and, in the second case, they are called membrane systems.

For the cover layer, usually films made of polyester, polypropylene, polyethylene, polyurethane, etc., are used which can also be metallized or pigmented. For the removable protective layer, among others, films made of polyester, polypropylene or even paper with silicone and/or polyethylene coating come into consideration.

For the active-ingredient-containing matrices which are usually used pharmaceutically or medically, polymer materials based on polyacrylate, silicone, polyisobutylene, butyl rubber, styrene/butadiene copolymer or styrene/isoprene copolymer are used.

The membranes used in the membrane systems can be microporous or semipermeable and are usually based on an inert polymer, especially polypropylene, polyvinyl acetate or silicone.

While the active-ingredient matrix compositions can be self-adhesive, depending on the active ingredient used, one can also have active-ingredient containing matrices, which are not self-adhesive, so that, as a consequence of this, the plaster or TTS must have an overtape in its structure.

In order to ensure the required flux rate of the active ingredient, frequently skin penetration enhancers are necessary as additives, such as aliphatic, cycloaliphatic and/or aromatic-aliphatic alcohols, which can be monovalent or polyvalent and may have up to 8 C-atoms, including an alcohol/water mixture, a saturated and/or unsaturated fatty alcohol with 8 to 18 carbon atoms, a saturated and/or unsaturated fatty acid with 8 to 18 carbon atoms and/or their esters, as well as vitamins.

Furthermore, frequently stabilizers such as polyvinylpyrrolidone, $\alpha$-tocopherol succinate, propyl gallate, methionine, cysteine and/or cysteine hydrochloride are added to the active-ingredient-containing matrix.

As the above discussion shows, numerous TTS structures and materials used for them are known. In any case, there are many interacting requirements to be considered when a drug is to satisfy medical requirements in the form of a TTS.

The following problems are to be considered fundamentally in the development of active-ingredient-containing TTS:

1. In order to achieve the therapeutically necessary penetration rates of the active ingredient through the skin, mostly a high load of active ingredient is required in the polymer matrix. After the end of application, the active ingredient remaining in the TTS is not used therapeutically and is disposed with the plaster. However, this is undesirable, especially in the case of highly active and expensive active ingredients for reasons of environmental protection and costs.

2. The polymer matrix which is loaded with the active ingredient and optionally additionally with skin penetration enhancers is not stable physically upon long storage. Especially, recrystallization of the active ingredient may occur, which leads to an uncontrollable decrease of the active-ingredient release capacity of the TTS.

3. High load of the polymer carrier with active ingredient and/or skin penetration enhancers makes the adjustment of optimum adhesive properties of the transdermal system difficult in the case of self-adhesive polymer films.

4. The resorption rate of the active ingredient decreases during application over several days in an unacceptable manner, so that additional control layers and/or control components are necessary.

5. If the active-ingredient-loaded layers are made from organic solutions, the problem arises that solvent residues remain in the active-ingredient-containing layer after the drying process. Additionally, there is a danger of undesirable evaporation of volatile additives during manufacture. Since, for reasons of physical stability and skin compatibility of the system, as a rule, an attempt must be made to have a system completely free from solvent, the reservoir therefore must be built up in several layers, as the case may be. This again leads to an increase of manufacturing costs.

Therefore, the problems described above require a large number of embodiments of Transdermal Therapeutic Systems, which are reflected in the state of the art in this field.

A more recent review on this is given, for example, in U.S. Pat. No. 5,662,926 (Wick et al., 1997). This document describes transdermal systems which contain a monolithic thermo plastic polymer film in which an active ingredient, preferably nicotine, is distributed homogeneously, as well as a method for solvent-free production of this active-ingredient-containing layer by mixing the active ingredient with the polymeric carrier material in the polymer melt, at temperatures from 170° C. to 200° C. In order to attach the active-ingredient-containing matrix film on the skin, there is an additional contact adhesive film which is applied onto the active ingredient matrix, and, if necessary, there is an additional plaster which has a larger area, and which is applied onto the active-ingredient-containing polymer film on the side of the matrix away from the skin.

Special pharmaceutical technical problems are to be solved in the development of estrogen plasters which must be applied for the treatment of climacteric complaints. The application should occur only once or twice per week. Increasing attention was received in this connection by the so-called 7-day plasters for reasons of cost and patient compliance in this indication. Cost aspects are of special importance here because many steroid sex hormones are highly costly drugs which are provided for continued therapy. In addition, when hormones are administered, for medical reasons, frequently a combination therapy is desired.

Thus, the natural estrogen—17β-estradiol—is usually administered for the treatment of climacteric complaints, either continuously or sequentially together with a gestagen.

An adequately known embodiment of such TTS is represented by monolithic active ingredient plasters, which make controlled release of the active components possible from a thin adhesive layer. However, in practice, the development of such active ingredient plasters with steroid sex hormones, especially when used over several days, encounters one or several of the difficulties outlined below, which frequently can be solved only by expensive measures and which increase the development and/or manufacturing costs. These are essentially the following problems:

1. The steroid sex hormone is released from the adhesive films at a relatively low rate per unit time through the skin, with the consequence that relatively large plasters must be applied in order to build up the therapeutically necessary hormone level in the blood over a long period of time and/or the so-called penetration accelerators must be administered together with the active ingredient(s) in order to achieve the required transepidermal transport rate.

2. The steroid sex hormone is physically unstable in the self-adhesive film, depending on the storage conditions, that is, there is especially the danger of recrystallization of an active ingredient during storage, which is related to uncontrollable decrease of the active ingredient release capacity.

3. The active ingredient resorption rate drops during use over several days in an unacceptable manner, so that additional control layers or control components are necessary.

4. High loading with active ingredient and penetration accelerators makes the optimum adjustment of the adhesive properties of the TTS difficult during development.

For example, cold flow of the self-adhesive reservoir layer represents special problems which, in human application, can lead to leakage of the active-ingredient-containing mass beyond the edge of the plaster and thus to the formation of dirty edges. Furthermore, partial or complete separation of the TTS, caused by the action of moisture (for example, during taking a shower, swimming, heavy sweating) and/or due to strong shear stresses as a result of muscular or skin movements, can be observed at the skin/plaster boundary.

5. Reservoir layers for the transdermal application are frequently prepared from solutions, so that the problem of remaining solvent residues in the active-ingredient-containing layer after the drying process and optionally the related evaporation and/or undesirable evaporation of volatile additives during manufacture occurs. In order to achieve complete absence of solvent, which should be strived for as a rule for reasons of physical stability and skin compatibility of the system, the reservoir should optionally be built from several layers, but this would lead to making the manufacturing process more expensive.

Regarding the transdermal application of estrogens and/or gestagens and/or androgens with the aid of monolithic systems, in which the active ingredient or ingredients are incorporated into a self-adhesive matrix, according to the state of the art—among others, because of their relatively good solvent properties for this group of active ingredients—preferably adhesives based on acrylate copolymers are used without (EP 0 416 8412, WO 93/10772) or with (WO 96/08255, DE 44 05 898) the addition of penetration-promoting, crystallization-inhibiting (WO 95/09618, WO 93/08795), active-ingredient solubility-enhancing (DE OS 44 05 898) and water-binding (DE 39 33 460) substances.

As a rule, the described formulations require the use of organic solvents, which must be removed again quantitatively during manufacture. Also, in spite of the relatively simple structure of monolithic TTS, the usual pharmaceutical quality requirements regarding adhesive properties, reproducibility of the active ingredient release and storage stability can only be provided with high technical expenditure for development and production because of the difficulties described above. Frequently, large-area plasters must be applied, especially for the administration of gestagens, in order to maintain the required active ingredient level in the blood over several days of application, as a result of which, first of all, the use properties and the related patient compliance become worse and, on the other hand, the cost of the preparation is increased further.

Furthermore, monolithic systems with sex steroids based on polystyrene block copolymers as carrier materials are known from the literature, the use of which permits in principle the production of self-adhesive active ingredient reservoirs from the melt without the use of organic solvents. Thus, in WO 94/26257, steroid-containing adhesives are described, which contain esters of colophonium and for which the manufacture of estradiol- and/or levonorgestrel-containing adhesive matrix can be done by melting and intensive kneading at high temperature over a long period of time. Transdermal Therapeutic Systems which are produced in this way have the disadvantage that the active ingredient (s) and/or pharmaceutical additives partially decompose under the conditions of the manufacturing process, that the adhesive properties and/or skin compatibility of the plaster over several days are insufficient and—especially for the gestagen component—the attainable plasma concentrations are therapeutically insufficient.

Furthermore, active ingredient plasters are known from EP 0 186 019 in which swellable polymers are added to a rubber adhesive mass in water and from which estradiol can be liberated, and, for which, in some individual cases, manufacture according to the hot-melt method is possible. With these formulations, it is still difficult to keep sufficient amounts of steroid sex hormones in the plaster matrix in solution and to release these over a long period of time at an approximately constant rate through the skin.

Furthermore, formulations are known from DE 44 29 667 for the transepidermal release of estradiol, which are produced without the use of organic solvents by melting the components of the formulation, with glycerol being added as protection against the precipitation of the estradiol hemihydrate during storage. The adhesive formulations, named in the Description and in the Examples, based on polystyrene block copolymers, correspond to the state of the art, that is, the active ingredient uptake and release capacity of TTS of this type are generally too low for application of the hormone plaster over several days, especially in the case of gestagens and androgens.

In addition to the monolithic system, multilayer matrix and reservoir systems are also adequately known from the literature, in which the active ingredient reservoir layer, adhesive layer and/or release-control layers are separated from one another functionally and/or spatially. EP 0 285 563 describes a TTS for the combined application of estrogens and gestagens. Here, the active ingredient reservoir contains ethanol as solvent and release-control agent for the active components. Furthermore, a membrane also participates in the control of the release of the steroidal hormones, being located between the reservoir and the separately arranged adhesive layer. The possible duration of application of such TTS depends, among others, greatly on the ethanol content in the reservoir (J. A. Simon et al. (1991), Fertility and Sterility, 56: 1029–1033), which, during application in humans, decreases continuously during resorption and thus limits the functional lifetime of the system. Since, in addition to the active ingredient, another component, which increases resorption, is also released at a relatively high rate, depending on the environmental, storage and application conditions, there is a risk of physical instability, decreasing adhesive force and/or local skin irritations.

A so-called "enhanced" system, in which, besides the active ingredient penetration accelerators are released on the skin and which contains separate reservoir, control and adhesive layers, is known and from the state of the art, again for the transepidermal application of testosterone (U.S. Pat. No. 5,152,997).

This TTS has the advantage for the patient that it does not have to be adhered to the relatively permeable scrotal skin, which is the case otherwise, due to the low absorption of the active ingredient in the case of testosterone plasters without penetration aid (for example, according to DE OS 35 23 065). However, application of such "enhanced" systems when used for more than 24 hours, is involves increased risk of local skin irritation, caused by the additives that control the skin permeation of testosterone. Especially in the case of unfavorable application conditions (perspiring, strong skin movements, showers), problems occur relating to the adhesion properties.

Finally, in the development of transdermal systems, polymers based on acrylic acid esters and methacrylic acid esters are of special interest because of their relatively good ability to take up and release a number of active ingredients. In order to avoid the use of solvents in the manufacture of matrix systems based on poly(meth)acrylate, DE 4310012 describes a dermal therapeutic system in which one or several layers are made of mixtures of poly(meth)acrylates and are produced from the melt, and the first mixing component consists of (meth)acrylate polymers which contain functional groups, the second mixing component controls the flow behavior and contains only insignificant amounts of functional groups. The composite systems with poly(meth)acrylates with functional groups are supposed to make it possible to have controlled release of the active ingredient(s) on or through the skin and facilitate simple manufacture. However, while there are advantages in the manufacture in comparison to solvent-based methods, according to experience, these systems exhibit a number of disadvantages and these are caused by the following:

1. Longer thermal exposure of all TTS components during (1) manufacture of the polymer melt, (2) homogeneous incorporation of the active ingredient or ingredients and/or (3) coating of the hot active-ingredient-containing mass onto suitable carrier materials, with an increased risk of degradation or decomposition reactions in the polymer melt and/or during storage of the active-ingredient-containing polymer films.

2. Difficulties in the optimization of the cohesion/adhesion balance of the poly(meth)acrylate-containing layer, since crosslinking of the acrylate copolymer with covalent bonds during manufacture of the active-ingredient-containing polymer matrix in the melt is not possible, in combination with problems that can arise because of cold flow of the polymer mass during application on the skin and/or during storage.

Strong bonding of the active ingredient/steroid hormones, especially of 17β-estradiol, in the polymer matrix by poly(meth)acrylates with a high content of free amino groups, as a result of which the flux rates of the sex steroid are reduced in comparison to poly(meth) acrylate matrices without free amino groups—at the same loading with active ingredient—(see FIG. 1, Comparison Example).

As the above list shows, many plaster constructions and materials used for these are known. Similarly, today there is still a great demand for many active ingredients that are incorporated into Transdermal Therapeutic Systems to have a TTS available, which makes it possible to provide the therapeutically required release of the active ingredient, without the construction being expensive and in which, overall, the components are in an optimal relationship.

This also applies to the active ingredient of the type of sex steroids when they are to be administered transcutaneously, especially to estrogens, gestagens and androgens.

Therefore, the task of the invention is to avoid the disadvantages of TTS with sex steroids described above and to provide a TTS for transepidermal administration of sex steroids alone or with other sex steroids with good adhesive properties, which is simple to construct, is compatible with the skin and is physically and chemically stable over a long duration of storage and application, and a) releases on and through the skin as much active ingredient as possible per unit area, b) is free from solvent and c) in which the active ingredient or ingredients used undergo as little thermal exposure as possible.

To solve this task, a steroid-hormone-containing TTS and a method for its preparation without the use of solvents is made available, the special composition of which surprisingly fulfills the tasks given above.

The Transdermal Therapeutic System (TTS) according to the invention contains a steroid-hormone-containing matrix mass in the form of a layer, in which the matrix mass has ammonium-group-containing (meth)acrylate copolymers, melt-extruded at 200° C. and also contains at least one plasticizer alone or in a mixture with an ethylene acrylate terpolymer and/or polyethylene glycol as well as at least 2 weight % of each of the steroid hormones present in the matrix mass without having been melted, and it is provided with a covering layer toward the outside. The laminate made of covering layer and steroid-containing matrix mass, with the exception of its release surface on the skin, is surrounded either by a larger active-ingredient-free skin plaster, which serves to attach the TTS to the site of application and/or for covering the active-ingredient-containing matrix at the open edges, or it has an active-ingredient-free adhesive film on the release surface. Advantageously, covalently crosslinkable acrylate copolymers or silicone-based polymers can be used as active-ingredient-free adhesive film. The release rates achievable with the TTS according to the invention are so high that the application time in comparison to the plaster system known from the state of the art can be lengthened, without increasing the application area (see FIG. 1).

In contrast to monolithic matrix systems, in the development of the TTS according to the invention, it is possible advantageously to optimize the cohesion/adhesion properties of the TTS on the one hand and the solubility dissolution rate and release behavior of the active ingredient on the other hand, largely separately. Furthermore, it is surprising regarding the TTS according to the invention that (1) at active ingredient concentrations in the polymer matrix, which are high in comparison to the state of the art, sufficient physical stability of the system is provided during long-term storage and that (2) the introduction of separate separating layers or membranes between the active-ingredient-containing layer and the active-ingredient-free layer can be omitted.

Surprisingly, in the type of TTS according to the present invention, the adhesion properties of the active-ingredient-containing matrix and the skin plaster provided as an attachment aid complement each other in such a way that immediately after adhesion of the TTS, an intimate contact is produced between the active-ingredient matrix and the skin, which is retained over several days even when using a relatively small-area skin plaster with an active-ingredient-free adhesive edge of about only 3.5 mm width, (Example: in the case of a square-shaped TTS with a total area of 20 cm$^2$, with rounded edges (including attachment aid) the area of the active-ingredient-containing matrix can be up to approximately 15 cm$^2$). If, according to the present invention, crosslinkable adhesive layers as attachment aid are coated directly onto the active ingredient layer, the self-adhesive TTS thus obtained, consisting of covering layer, active-ingredient layer and adhesive layer also provide surprisingly high steroid release rates over a long period of application (see FIG. 1, Example 2).

In spite of the high loading of the matrix mass with at least 2 weight % of active ingredient(s), due to the special qualitative and quantitative composition of the matrix mass, no tendency of the incorporated active ingredients to recrystallization is observed, although, especially in the case of hormone-containing plasters, the sensitivity to moisture is a great problem. As a result of this, the active adhesive surface of the TTS can be kept small, the functional lifetime of the TTS can be extended and thus patient compliance can be taken into consideration. Surprisingly, more than 10 weight % of NETa (=norethisterone acetate) can be incorporated into the matrix mass.

Furthermore, it was surprising that in the matrix composition according to the invention, tributyl citrate is especially advantageous as plasticizer.

The embodiment according to the invention, in which the steroid-hormone-containing matrix mass is a solid solution is especially advantageous.

Furthermore, a TTS according to the invention may contain estrogens or gestagens alone or in combinations of these.

Finally, a TTS according to the invention may contain androgens in an embodiment.

Advantageously, the carrier film used for the TTS on the matrix side has a metal vapor or metal oxide coating.

In the sense of the invention the following terms are defined as given below:

a) "solvent-free": no solvent is used for the manufacture of the polymer matrices which solvent would have to be removed again largely during the manufacturing process, as it is done in the "solvent-based" method.

b) "longer application time period": The TTS can be applied to the skin for therapeutic application for up to 7 days.

c) "solid solution": The pharmaceutical active ingredient is present in the plaster matrix in the molecularly dispersed form.

d) "transepidermal": Same meaning and function as transcutaneous e) "thermally minimally exposed active ingredient": The active ingredient is added without melting to the matrix mass which was heated by melt-extrusion, which is then cooled after the addition of the active ingredient.

The method of the production of the TTS according to the invention is characterized by the fact that a coatable steroid-hormone-containing matrix mass is produced by melt-extrusion, in which the active components are weighed and incorporated continuously without premelting into the hot polymer melt heated up to 200° C., the hot active-ingredient-containing polymer melt is then coated directly onto a separable protective layer (=substrate) to a thickness of 0.02 to 0.4 mm and then the obtained 2-layer laminate is covered with a cover layer. To attach the active ingredient matrix on the skin and/or to cover the matrix at the open edges, one can use a larger active-ingredient-free skin plaster or an active-ingredient-free adhesive film made of a crosslinked acrylate copolymer can be laminated directly onto the active-ingredient-containing polymer matrix. The TTS according to the invention are provided with a protective film which is removed before application of the preparation onto the skin.

An essential advantage of the method according to the invention consists in the fact that the active ingredient reservoir (I) is produced without the use of organic solvents and (II) the preparation of the active-ingredient-containing matrix mass and its further processing to an active-ingredient-containing layer is done in a continuous and especially cost-saving process. The process times can be shortened to a few minutes and thus, at the same time, the danger of decomposition reactions in the active-ingredient-containing polymer melt can be reduced to a minimum. Surprisingly, it was found that the complete dissolution of the sex steroid(s) in the polymer melt is provided in spite of the short processing times under the process conditions explained further in the Examples.

Furthermore, as a result of the continuous manufacture of the steroid-hormone-containing polymer mass, scaling-up problems are avoided. That is, in order to increase the batch size or charge size, no changes are necessary from larger production installations for the manufacture of the active-ingredient-containing polymer melt or of the laminate, which usually requires time-consuming and expensive installation, qualification and validation work as well as optionally also changes in the formulation.

The invention will be explained below with the aid of Examples:

A) TTS, WHICH ARE LOADED WITH ONE ACTIVE INGREDIENT

I. EXAMPLE 1

A two-screw extruder equipped with three dosage units is charged continuously in successive process zones with Eudragit RS 100 (copolymer of ethyl acrylate and methyl methacrylate with approximately 5% trimethylammonium ethyl methacrylate chloride), tributyl citrate (TBC) and 17β-estradiol hemihydrate, and the mixture is melt-extruded at a total throughput of 150 g of mass/minute at a temperature of 130–150° C. From dosage unit 1, Eudragit RS 100 is introduced to the process part of the extruder at a rate of 97.2 g/minute, from dosage unit 2, tributyl citrate is introduced at a rate of 45.82 g/minute and finally, from dosage unit 3, 17β-estradiol hemihydrate is introduced at a row [sic, should be rate] of 6.975 g/minute. After leaving the extruder, the obtained hot estradiol-polymer melt is introduced through a heated inlet tubing in a continuous stream directly to the discharge head of the coating installation and, with the aid of a slit-shaped nozzle, is laminated onto an approximately 100 μm thick siliconized polyester film (=protective film), in such a way that the area weight of the active-ingredient-containing matrix layer is approximately 80 g per m². After going through a roll cooling device, the two-layer laminate is covered with an approximately 20 micrometer thick polyester film (=carrier film). The web-shaped three-layer laminate thus obtained is rolled up onto rolls and then 8 cm² pieces are stamped out of it. The resulting TTS contain approximately 2.88 mg of 17β-estradiol calculated as hemihydrate. For application on the skin, after removal of the siliconized polyester film, a 16 cm² active-ingredient-free skin plaster ("overtape"), consisting of an adhesive film based on a cross linked acrylate copolymer and a carrier film, is adhered over the TTS.

II. EXAMPLE 2

(1) Preparation of the Active-ingredient-containing Reservoir Layer

The preparation of the active-ingredient-containing reservoir layer is done by melt-extrusion and hot-melt coating, as described in Example 1.

(2) Preparation of the Active-ingredient-free Adhesive Film 750 g of a solution of a crosslinkable adhesive based on acrylate copolymer with at least one derivative of acrylic and methacrylic acid (for example, Duro-Tak 87-2852) are coated with a doctor-blade applicator onto an approximately 100 μm thick polyester film which is coated on one side with evaporated aluminum and on both sides with silicone, so that after the removal of the solvent at 40 to 80° C. and a drying time of approximately 18 minutes, an active-ingredient-containing [Sic, should be active-ingredient-free—Translator] adhesive film with an area weight of 20 g/m² results.

(3) Preparation of TTS

On the active-ingredient-free adhesive film obtained according to (2), the reservoir layer from (1) is coated after removal of the protective film and the resulting 4-layer laminate, consisting of protective film, adhesive film, active-ingredient-containing matrix layer and carrier film, is stamped into 10 cm² pieces. The self-adhesive TTS thus obtained contain approximately 3.6 mg of 17β-estradiol, calculated as hemihydrate.

III. COMPARISON EXAMPLE (Polymethacrylate Mixture in the Composition Corresponding to DE 43 10 012)

A two-screw extruder equipped with four dosage units is charged in successive process zones with Eudragit RS 100 (copolymer of ethyl acrylate and methyl methacrylate with approximately 5% trimethylammonium methacrylate chloride), Eudragit E 100 (copolymer of butyl methacrylate, methyl methacrylate and 2-dimethylaminoethyl methacrylate with an amino group content of 25%), tributyl citrate (TBC) and 17β-estradiol hemihydrate. The mixture is melt-extruded at a total throughput of 150 g/minute at a temperature of 130–150° C. Eudragit RS 100 (1) and Eudragit E 100 (2) are applied with the aid of dosage units 1 and 2, respectively, at a rate of (1) 42.75 g/minute and (2) 59.85 g/minute into the first process zone of the extruder. In the next two following process zones, TBC is applied with the aid of dosage unit 3 at a rate of 39.9 g/minute and estradiol hemihydrate with dosage unit 4 at a rate of 7.5 g/minute. The further processing is done according to Example 1, whereby, the 3-layer laminate obtained after the coating, in webs, consisting of protective film, active-ingredient-containing matrix with an area weight of 80 g/minute² and a carrier film, is stamped into pieces of 16 cm² in size. The resulting self-adhesive TTS contain approximately 6.4 mg of 17β-estradiol, calculated as the hemihydrate.

IV. IN-VITRO INVESTIGATIONS

Estradiol Flux Measurements In Vitro

In order to evaluate the liberation of active ingredient in vitro, a TTS with a stamped area of 5 cm² is secured in a modified Franz diffusion cell on a skin preparation from hairless mice. Immediately afterwards, the cell is filled with distilled water as a release medium, free from air bubbles, and is thermostated at 37±0.5° C.

At the sampling times, the release medium is replaced by fresh water thermostated to 37±0.5° C.

The estradiol content in the removed release medium is determined with the aid of high-performance liquid chromatography. The results of the investigations are given in Table 1 for Examples 1 and 2, as well as for the Comparison Example and a commercial matrix plaster with a declared release of 50 μg of estradiol per day. As comparison of the flux rates shows, the TTS according to the invention releases clearly more estradiol through the skin than the comparison systems.

TABLE 1

Estradiol flux rates

| TTS | estradiol content (hemihydrate) mg/cm$^2$ | weight % | cumulative flux rate (μg/cm$^2$), mean values, n = 3 | | |
|---|---|---|---|---|---|
| | | | after 24 h | 48 h | 72 h |
| Example 1 | 0.36 | 4.65 | 74.2 | 131.6 | 171.1 |
| Example 2 | 0.36 | 3.72 | 33.1 | 71.0 | 104.4 |
| Comparison Example (DE 43 10 012) | 0.40 | 5.00 | 24.0 | 48.0 | 70.5 |
| Commercial preparation (matrix plaster) | 0.20 | 2.50 | 22.9 | 38.8 | 51.8 |

V. BIOAVAILABILITY OF ESTRADIOL FROM THE TSS ACCORDING TO THE INVENTION

In an open human pharmacological study, the estradiol bioavailability was tested on 8 post-menopausal women in a 4-fold cross-over study design with the TTS shown in Table 1. Each type of TTS was applied over a time period of 6 days with repeated administration, that is, plaster change after 3 days. Corresponding to the number of comparison and test preparations, a total of 4 treatments, each with 2 directly following plaster applications, were performed.

The wash-out phase between 2 treatments was at least one week. In order to determine the transepidermal resorbed active ingredient amounts, blood was taken from the test subjects at specified time intervals. A sensitive GC/MS method (quantification limit: 5 pg/mL) served for the quantitative determination of the estradiol concentration in the blood plasma.

The time-dependent, area-normalized course of the obtained estradiol plasma concentrations over 6 days (each with a TTS change after 3 days) is shown in FIG. 1 for the test plasters and comparison plasters. As can be seen from the Figure, with the TTS according to the invention, clearly higher estradiol levels were achieved in the plasma per unit area in comparison to the TTS corresponding to the Comparison Example and the tested commercial preparation.

B) TTS, WHICH ARE CHARGED WITH MORE THAN ONE ACTIVE INGREDIENT

EXAMPLE 3

A two-screw extruder equipped with four dosage units is charged continuously in successive process zones with Eudragit RS 100 (copolymer of ethyl acrylate and methyl methacrylate with approximately 5% trimethylammonium ethyl methacrylate chloride, tributyl citrate (TBC), 17β-estradiol hemihydrate and norethisterone acetate, with the mixture being melt-extruded at a total throughput of 116.7 g of mass/minute at a temperature of 130–150° C. From dosage unit 1, Eudragit RS 100 is introduced at a rate of 62.24 g/minute to the process part of the extruder, from dosage unit 2, tributyl citrate was introduced at a rate of 29.34 g/minute, from dosage station 3, 17β-estradiol hemihydrate was introduced at a rate of 4.667 g/minute and finally, from dosage station 4, norethisterone acetate was introduced at a rate of 20.417 g/minute. After leaving the extruder, the obtained hot estradiol-norethisterone acetate-polymer melt was introduced through a heatable feed tubing directly in a continuous stream to the discharge head of the coating installation and laminated with the aid of a slit-shaped nozzle onto an approximately 100 μm-thick siliconized polyester film (=protective film) in such a way that the area weight of the reservoir layer is approximately 80 g per μm. Then, after going through a roll cooling device, the two-layer laminate is covered with an approximately 20 micrometer thick polyester film (=carrier film). The web-shaped three-layer laminate thus obtained is rolled onto rollers and then stamped to 16 cm$^2$ pieces. The resulting TTS reservoirs contain approximately 5.12 mg of 17β-estradiol, calculated as hemihydrate and approximately 22.40 mg of norethisterone acetate. For application onto the skin, after removal of the siliconized polyester film, the TTS are covered with a 32 cm$^2$ active-ingredient-free skin plaster ("overtape"), consisting of an adhesive film based on a crosslinked acrylate copolymer and a carrier film.

TABLE 4

Flux rates of estradiol (E2)- and norethisterone acetate (NETa) through excised mouse skin

| Example 6 | active ingredient content | | cumulative flux rates μg/cm$^2$, mean values, n = 3 | | |
|---|---|---|---|---|---|
| | mg/cm$^2$ | weight % | after 24 h | after 48 h | after 72 h |
| E2 (hemihydrate) | 0.3 | 4.0 | 16.0 | 33.2 | 48.9 |
| NETa | 1.4 | 17.5 | 34.3 | 73.9 | 114.5 |

In-vitro Investigations

The determination is carried out as described under II. The measured flux rates are given in Table 4, together with the active ingredient content of the test sample. As can be seen from Table 4, with the method according to the invention, combination TTS with a high NETa content and a high flux rate through the excised skin preparations can be produced.

What is claimed is:

1. A transdermal therapeutic system for transcutaneous administration of sex steroids over a period of up to seven days having an attachment aid for the system onto skin, wherein the system comprises a layer-form of a sex steroid-containing matrix mass disposed on a carrier film, and said matrix mass comprising a solid solution of (a) a copolymer of ethyl acrylate and methyl methacrylate containing about 5% trimethylammonium ethyl methacrylate chloride as the sole (meth)acrylate copolymer, (b) about 25 weight percent to about 30.5 weight percent of at least one plasticizer, (c) an optional ethylene acrylate terpolymer, and (d) at least 2 weight percent of each sex steroid distributed in a molecularly dispersed form in the matrix mass, said sex steroid selected from the group consisting of an androgen, an estrogen, a gestagen, and a mixture of an estrogen and a gestagen, and surrounded by a larger active-ingredient-free plaster for attachment to an application site, with the exception of a release surface on the skin, wherein at least one sex steroid underwent a minimum thermal exposure, and wherein the system is free of a rate-controlling polymer layer for delivery of the sex steroids.

2. The system of claim 1 wherein on the edge, onto the steroid-hormone-containing matrix mass, an active-ingredient-free adhesive film comprising crosslinked acrylate copolymers is applied for attaching the steroid hormone-containing matrix onto the skin.

3. The system of claim 1 wherein the steroid-hormone-containing matrix contains citric acid triester as the plasticizer.

4. The system of claim 1 wherein the system contains an estrogen, a gestagen, or a mixture thereof.

5. The system of claim 1 wherein the system contains androgens.

6. The system of claim 1 wherein the carrier film has a metal vapor or metal oxide coating on the matrix side.

7. A method of producing a transdermal therapeutic system of claim 1 comprising:

(a) providing an extruder having a first inlet port for introducing a copolymer of ethyl acrylate and methyl methacrylate containing about 5% trimethylammonium ethyl methacrylate chloride as the sole (meth)acrylate copolymer, a second inlet port for introducing the plasticizer, and a sufficient number of inlet ports for introducing each sex steroid;

(b) continuously coextruding the ethyl acrylate and methyl methacrylate copolymer, plasticizer, and sex steroids at 130° C. to 150° C. for a sufficiently short time to maintain the sex steroids in a nonmolten form as a laminate matrix mass of thickness 0.02 to 0.4 mm onto a protective film; and (c) applying a carrier film on a surface of the laminate matrix mass opposite from the protective film.

8. The method of claim 7 wherein the plasticizer comprises tributyl citrate.

9. The method of claim 7 wherein the steroid hormone comprises 17β-estradiol, norethisterone acetate, or a mixture thereof.

10. The method of claim 7 wherein the protective film comprises a silicone-coated polyester film.

11. The method of claim 7 wherein the carrier film comprises a polyester film.

12. A transdermal therapeutic system for transcutaneous administration of sex steroids a period of up to seven days having an attachment aid for the system onto skin, wherein the system comprises a layer-form of a sex steroid-containing matrix mass disposed on a carrier film, and said matrix mass consisting essentially of a solid solution of (a) a copolymer of ethyl acrylate and methyl methacrylate containing about 5% trimethylammonium ethyl methacrylate chloride as the sole (meth)acrylate copolymer, (b) about 25 weight percent to about 30.5 weight percent of at least one plasticizer, and (c) at least 2 weight percent of each sex steroid distributed in a molecularly dispersed form in the matrix mass, said sex steroids selected from the group consisting of an androgen, an estrogen, a gestagen, and a mixture of an estrogen and a gestagen, and surrounded by a larger active-ingredient-free plaster for attachment to an application site, with the exception of a release surface on the skin wherein the sex steroids underwent a minimum thermal exposure, and wherein the system is free of a rate-controlling polymer layer for delivery of the sex steroids, wherein said system is prepared by a method comprising:

(a) providing an extruder having a first inlet port for introducing the copolymer of ethyl acrylate and methyl methacrylate containing about 5% trimethylammonium ethyl methacrylate chloride, a second inlet port for introducing the plasticizer, and a sufficient number of inlet ports for introducing each sex steroid;

(b) continuously coextruding the copolymer of ethyl acrylate and methyl methacrylate containing about 5% trimethylammonium ethyl methacrylate chloride, plasticizer, and sex steroids at 130° C. to 150° C. for a time sufficiently short to maintain the sex steroids in a nonmolten form as a laminate matrix mass of thickness 0.02 to 0.4 mm onto a protective film; and (c) applying a carrier film on a surface of the laminate matrix mass opposite from the protective film.

* * * * *

UNITED STATES PATENT AND TRADEMARK OFFICE
CERTIFICATE OF CORRECTION

PATENT NO. : 6,562,367 B1  Page 1 of 1
DATED : May 13, 2003
INVENTOR(S) : Hans-Michael Wolff et al.

It is certified that error appears in the above-identified patent and that said Letters Patent is hereby corrected as shown below:

<u>Column 3,</u>
Line 39, "thermo plastic" should be -- thermoplastic --

<u>Column 9,</u>
Lines 55-56, "is introduced at a row" should be -- is introduced at a rate --

<u>Column 10,</u>
Lines 24-25, "active-ingredient-containing" should be -- active-ingredient-free --

Signed and Sealed this

Fourteenth Day of October, 2003

JAMES E. ROGAN
*Director of the United States Patent and Trademark Office*